United States Patent
Hartley

(10) Patent No.: US 10,206,663 B2
(45) Date of Patent: Feb. 19, 2019

(54) APPARATUS FOR DRAWING OF A BODILY FLUID AND METHOD THEREFOR

(71) Applicant: Frank Thomas Hartley, Arcadia, CA (US)

(72) Inventor: Frank Thomas Hartley, Arcadia, CA (US)

(73) Assignee: Roc8Sci Co., Arcadia, CA (US)

( * ) Notice: Subject to any disclaimer, the term of this patent is extended or adjusted under 35 U.S.C. 154(b) by 118 days.

(21) Appl. No.: 14/996,089

(22) Filed: Jan. 14, 2016

(65) Prior Publication Data

US 2016/0199042 A1   Jul. 14, 2016

Related U.S. Application Data

(60) Provisional application No. 62/125,105, filed on Jan. 14, 2015, provisional application No. 62/197,298, filed on Jul. 27, 2015.

(51) Int. Cl.
*A61B 5/15*   (2006.01)
*B01L 3/00*   (2006.01)
(Continued)

(52) U.S. Cl.
CPC .... *A61B 10/0045* (2013.01); *A61B 5/150022* (2013.01); *A61B 5/15105* (2013.01); *A61B 5/15142* (2013.01); *A61B 5/150251* (2013.01); *A61B 5/150343* (2013.01); *A61B 5/150389* (2013.01); *A61B 5/150503* (2013.01); *A61B 5/150755* (2013.01); *B01L 3/50273* (2013.01);
(Continued)

(58) Field of Classification Search
CPC ............ A61B 5/150419; B01L 3/5027; B01L 2400/0406; B01L 2200/027
See application file for complete search history.

(56) References Cited

U.S. PATENT DOCUMENTS 5,674,457 A   10/1997  Williamsson et al.
5,801,057 A   9/1998   Smart et al.
(Continued)

OTHER PUBLICATIONS

Authorized Officer: Lee W. Young, "International Search Report and Written Opinion of the International Searching Authority" dated May 11, 2016 in counterpart International PCT Application PCT/US16/13481.

*Primary Examiner* — Devin B Henson
*Assistant Examiner* — Huong Q. Nguyen
(74) *Attorney, Agent, or Firm* — Kaplan Breyer Schwarz, LLP

(57) ABSTRACT

A sample holder that enables mid-infrared spectroscopy of a test sample using mid-infrared light is disclosed. The sample holder includes an inlet port and a sample chamber that comprises a sample region and a capillary channel that fluidically couples the inlet port and the sample region. The capillary channel is characterized by a higher capillary force than the sample region. As a result, when the inlet port is put in contact with a liquid containing the test sample, the liquid is drawn into the sample region without the formation of bubbles that could obscure the optical analysis. In some embodiments, the inlet port is the free end of a draw tube having an outer diameter that is smaller than the minimum spacing between pain receptors at a draw site on a patient, which mitigates pain felt by the patient due to insertion of the draw tube at the draw site.

19 Claims, 13 Drawing Sheets

(51) Int. Cl.
 *A61B 10/00* (2006.01)
 *A61B 5/151* (2006.01)
(52) U.S. Cl.
 CPC ... *B01L 3/502715* (2013.01); *B01L 2200/027* (2013.01); *B01L 2200/0684* (2013.01); *B01L 2300/0645* (2013.01); *B01L 2300/0681* (2013.01); *B01L 2300/0816* (2013.01); *B01L 2300/0838* (2013.01); *B01L 2300/0858* (2013.01); *B01L 2400/0406* (2013.01)

(56) References Cited

U.S. PATENT DOCUMENTS

| | | | |
|---|---|---|---|
| 6,451,264 B1* | 9/2002 | Bhullar | B01L 3/502746 204/451 |
| 7,822,454 B1* | 10/2010 | Alden | A61B 5/14532 600/345 |
| 2003/0040683 A1* | 2/2003 | Rule | A61B 5/14532 600/584 |
| 2003/0138823 A1* | 7/2003 | Brock | B82Y 30/00 435/6.11 |
| 2003/0171696 A1* | 9/2003 | Dosmann | A61B 5/1411 600/583 |
| 2003/0212346 A1* | 11/2003 | Yuzhakov | A61B 5/1411 600/584 |
| 2005/0244954 A1* | 11/2005 | Blackburn | B01L 3/502753 435/287.2 |
| 2010/0032298 A1 | 2/2010 | Reel et al. | |
| 2010/0074801 A1* | 3/2010 | Saiki | B01L 3/502715 422/68.1 |
| 2011/0033338 A1* | 2/2011 | Cho | B01L 3/502707 422/68.1 |
| 2012/0122084 A1 | 5/2012 | Wagner et al. | |
| 2014/0219886 A1 | 8/2014 | Choi et al. | |
| 2014/0275866 A1* | 9/2014 | Gunnerson | A61B 5/14507 600/309 |

* cited by examiner

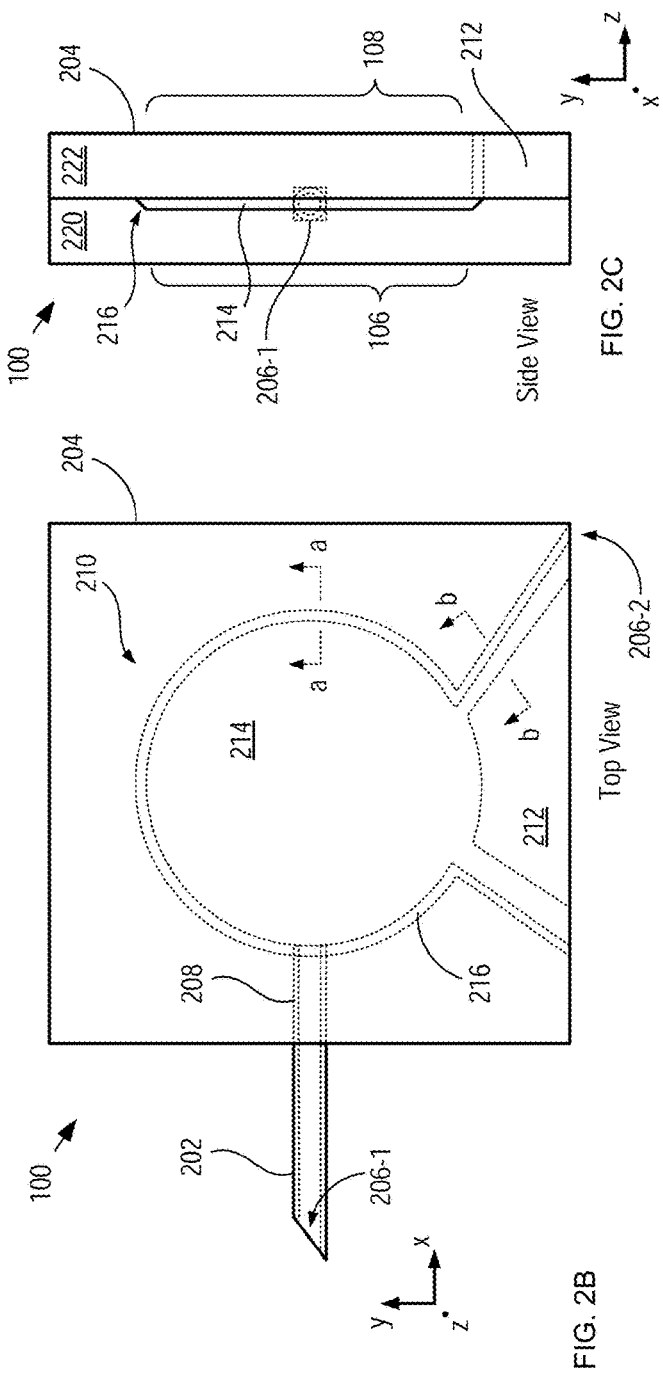

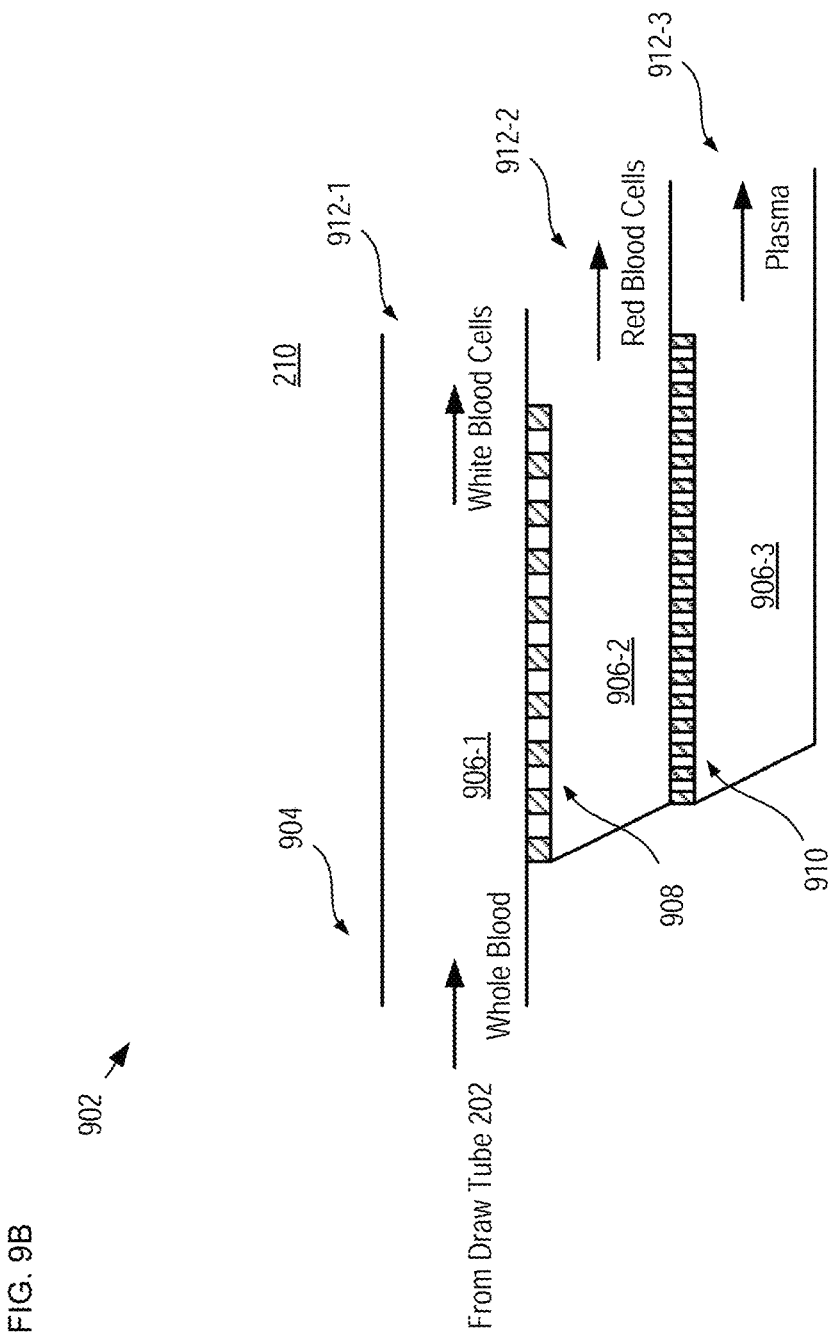

APPARATUS FOR DRAWING OF A BODILY FLUID AND METHOD THEREFOR

CROSS REFERENCE TO RELATED APPLICATIONS

This application claims the benefit of U.S. Provisional Application Ser. No. 62/125,105, filed Jan. 14, 2015, entitled "Methods for the Painless Drawing of Aliquots of Bodily Fluids and Their Analytics," and U.S. Provisional Application Ser. No. 62/197,298, filed Jul. 27, 2015, entitled "A Micro-Cuvette for the Painless Drawing of Aliquots of Bodily Fluids and Their Optical Analysis," each of which is incorporated herein by reference. If there are any contradictions or inconsistencies in language between this application and one or more of the cases that have been incorporated by reference that might affect the interpretation of the claims in this case, the claims in this case should be interpreted to be consistent with the language in this case.

FIELD OF THE INVENTION

The present invention relates to analytical chemistry technology in general, and, more particularly, to chemical analysis of fluids and fluid-like materials.

BACKGROUND OF THE INVENTION

An assessment of patient health is often based, in part, on the chemistry of one or more bodily fluids of that patient, such as blood, urine, spittle, tears, etc. Blood, for example, provides many key health markers, for example, such as hemoglobin (red blood cell) count, white-blood-cell (WBC) count, nitrogen level, glucose level, and ion concentration, among others.

Unfortunately, the collection of bodily fluids in volumes sufficient for reliable testing can be challenging. For example, conventional blood-test samples are usually drawn in-vivo using large medical syringes, which can cause significant patient distress—before, during, and after the drawing procedure.

Blood drawing methods are highly manual in nature and typically require trained personnel who can properly select a vein suitable for needle insertion and extract the blood into one or more sample vials. It is not uncommon that, during a blood draw, the skin is punctured but the target vein is missed. In such cases, the needle must be removed and reinserted in a second attempt to hit the proper vein. In other cases, the needle is inserted into the target vein too deeply. As a result, the other end wall of the target vein is punctured, which can cause blood leakage under the skin to give rise to a hematoma.

To avoid some of the complications of in-vivo blood drawing, a blood sample can be acquired ex-vivo using a lancelet to puncture the skin at a location that can provide a sufficient amount of blood—typically, a fingertip. Unfortunately, this method also has many disadvantages. First, lancelet-based blood drawing typically yields only a small amount of blood before clotting occurs. The presence of a blood clot in a blood sample is a cause for rejection of the sample because testing of partially clotted blood can lead to irregularities in some blood tests. Second, sites that are prone to provide more blood when pierced also tend to have a high concentration of pain receptors. As a result, a puncture of the skin at these sites typically causes the patient more pain.

Both blood-drawing methods cause significant pain to the patient, weep internally and externally afterward, give rise to potential infection sites, and are prone to bruising and prolonged tenderness. As a result, patients are understandably unenthusiastic about having their blood drawn.

Further, a typical test panel requires several milliliters (or tens of milliliters) of blood. This is true for other bodily fluids—urine, spittle, synovial fluid, moist solids, etc., which, in many cases, can be difficult to collect from the patient in sufficient volume.

The need to enable sophisticated analysis of a bodily fluid using only a small volume of fluid and without subjecting a patient to significant pain or risk of complication remains, as yet, unmet.

SUMMARY OF THE INVENTION

The present invention enables analysis of a test sample without some of the costs and disadvantages of the prior art. Embodiments of the present invention enable content-rich analysis of small-volume test samples of liquids or moist solids, such as chemical solutions, petroleum products (e.g., fuel oils, crude oil, waste oils, etc.), bodily fluids (e.g., blood, urine, spittle, sweat, tears, saliva, stool, etc.), foodstuffs (e.g., dairy products, pastes, sauces, etc.), cosmetic compounds, and the like, thereby obviating the need for drawing and storing large volumes of material.

The present invention encompasses two key inventive aspects: 1) a sample holder that is easy to fabricate and low cost, but that enables spectroscopic analysis of a test sample using mid-infrared radiation; and 2) a microfluidic system that is dimensioned and arranged to facilitate the rapid filling of a chamber with a liquid without inducing bubbles in the liquid, where the force that draws the liquid into the chamber is capillary force.

An illustrative embodiment of the present invention is a compact sample holder operative for drawing blood from a draw site on a patient via capillary force and without causing bubbles to form during the draw. The sample holder comprises a draw tube and a small-volume, two-part sample chamber, which includes a sample region and a capillary channel. The sample holder is transmissive for mid-infrared radiation, which enables spectroscopic analysis of the blood over a short interaction length with the test sample. As a result, the sample holder requires only a small-volume sample chamber, which mitigates the need for drawing large volumes of blood from the patient. The patient, therefore, is not subjected to significant pain, discomfort, or long draw times.

The draw tube is a stainless-steel hypodermic needle having an outer diameter that is approximately 125 microns—smaller than the normal minimum spacing of pain receptors in the human body. The inner diameter of the draw tube is approximately 50 microns, which gives rise to two-phase flow of blood through the draw tube, wherein blood cells are concentrated in the central region of the flow while a sheath of plasma flow surrounds the blood cells.

The draw tube is fluidically coupled with sample region via the capillary channel, which extends around the perimeter of the sample region. The sample chamber is formed in a body that is made of float-zone silicon. Because float-zone silicon is substantially transparent to mid-infrared radiation, by virtue of its extremely low impurity concentration, its use as the structural material of the body enables sample analysis using mid-infrared light, which is a spectral-information-rich wavelength region for most biological materials. In some embodiments, a different material that is substantially transparent to mid-infrared light is used as the structural material. In some embodiments, the body enables spectroscopic analysis of the test sample using radiation other than mid-infrared radiation and the sample chamber is transmissive for that radiation.

The sample chamber is a circular region having a volume that is equivalent to approximately $\frac{1}{50}^{th}$ of a drop of blood. It is defined by top and bottom surfaces that are closely spaced and substantially parallel, and a sidewall that is oriented an angle of approximately 45° to the top and bottom surfaces. The spacing of the top and bottom surfaces in the sample region enable development of capillary force for drawing liquid into the sample region, while the bottom surface and the sidewall collectively define a small triangular cross-section for the capillary channel, which fluidically couples the sample chamber with the draw tube. The small cross-sectional spacing of the sample region and capillary channel gives rise to a strong capillary force that enhances the capillary drawing capability of the sample holder and inhibits the formation of bubbles in the sample as it is drawn into the sample chamber. In some embodiments, the angle of the sidewall, with respect to the top and bottom surfaces, is less than 45°. In some embodiments, the sidewall is a non-planar surface.

In some embodiments, the sample holder does not include a draw tube but, instead, draws liquid through an inlet port located on a side of the body.

An illustrative method for analyzing a sample of bodily fluid comprises: drawing the sample into the sample chamber via capillary force, transmitting mid-infrared light through the body and sample, detecting the spectrum of the light after it has passed through the sample, removing the contribution of the absorption spectrum of water from the measured absorption spectrum of the sample, and comparing the resultant normalized spectrum to stored spectra for one or more analytes of interest.

In some embodiments, the sample region includes one or more regions that are functionalized with a reagent that gives rise to a visible signal based on an analyte of interest.

In some embodiments, the sample chamber includes a microfluidic system that includes one or more microfluidic elements, such as filters, mixers, separators, and the like.

In some embodiments, the body includes an optical element, such as a diffractive element, holographic element, refractive lens, and the like.

In some embodiments, the sample chamber includes one or more electrodes that enable electrochemical analysis of the sample.

An embodiment of the present invention is a sample holder for holding a test sample, the sample holder comprising: an inlet port; and a sample chamber that includes a first surface that is transmissive for radiation having a wavelength within the range of approximately 2.5 microns to approximately 12.5 microns, the sample chamber having a sample region and a capillary channel that fluidically couples the inlet port and the sample region; wherein the sample region is characterized by a first capillary force for a first liquid and the capillary channel is characterized by a second capillary force for the first liquid, and wherein the second capillary force is higher than the first capillary force such that the capillary channel is operative for drawing the first liquid from the inlet port to the sample chamber; and wherein the first liquid includes the test sample.

Another embodiment of the present invention is a sample holder for holding a test sample, the sample holder comprising: a body comprising float-zone silicon that is transmissive for radiation having a wavelength within the range of approximately 2.5 microns to 12.5 microns the body including: a first surface; a second surface that is substantially parallel with the first surface, wherein the first surface and second surface are separated by a first separation; and a sidewall that extends from the first surface to the second surface; wherein the first surface, the second surface, and the sidewall collectively define a sample chamber having (1) a sample region having a volume that is less than or equal to one microliter and (2) a capillary channel having a first width; and wherein the sidewall and second surface are separated by a second separation that changes monotonically from zero to the first separation along the first width; and an inlet port that is fluidically coupled with the sample region by the capillary channel; wherein the capillary channel is dimensioned and arranged to induce a capillary force operative for drawing a liquid from the inlet port into the sample region.

Yet another embodiment of the present invention is a method comprising: providing a sample holder for a test sample, the sample holder including a body comprising a first material that is transmissive for radiation having a wavelength within the range of approximately 2.5 microns to approximately 12.5 microns, and the sample holder having an inlet port and a sample chamber that includes a sample region and a capillary channel, wherein the capillary channel fluidically couples the inlet port and the sample region; and establishing physical contact between the inlet port and a liquid that contains the test sample; wherein physical contact between the inlet port and the liquid gives rise to a capillary force that draws the test sample into the sample chamber via the capillary channel.

BRIEF DESCRIPTION OF THE DRAWINGS

FIGS. 2A-D depict schematic drawings of perspective, top, side, and front views, respectively, of sample holder 100.

FIG. 9B depicts a schematic drawing of microfluidic system 902.

DETAILED DESCRIPTION

The following terms are defined for use in this Specification, including the appended claims:

"Mid-infrared radiation" (MIR) is defined as electromagnetic radiation having a wavelength within the range of approximately 2.5 microns to approximately 12.5 microns.

"Transmissive" is defined as having a transmission of at least 45%. For example, an element that is transmissive for mid-infrared radiation transmits at least 45% of any light signal having a wavelength within the range of approximately 2.5 microns to approximately 12.5 microns.

Figure 1:
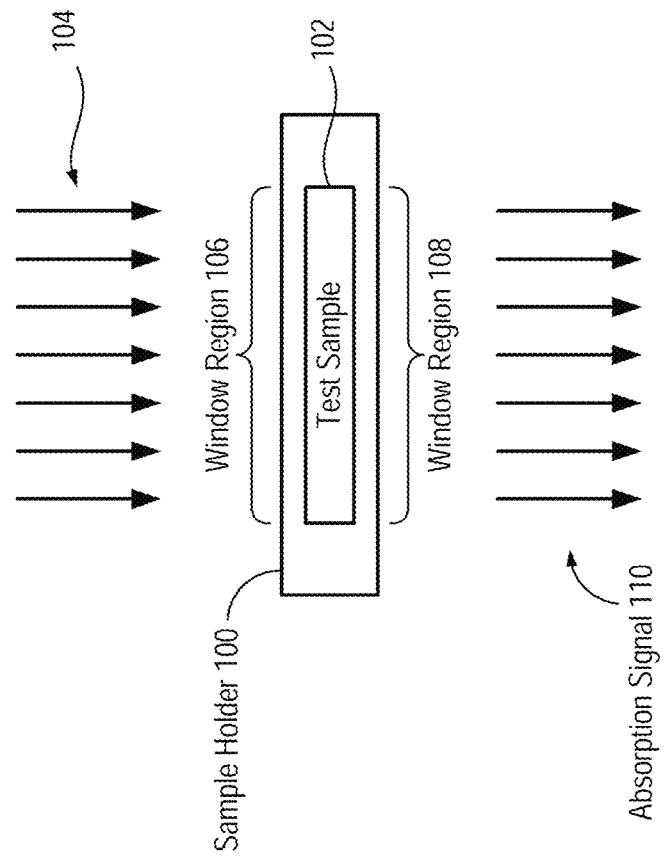
FIG. 1 depicts a schematic drawing of a sample holder in accordance with an illustrative embodiment of the present invention.
Figure 2A:
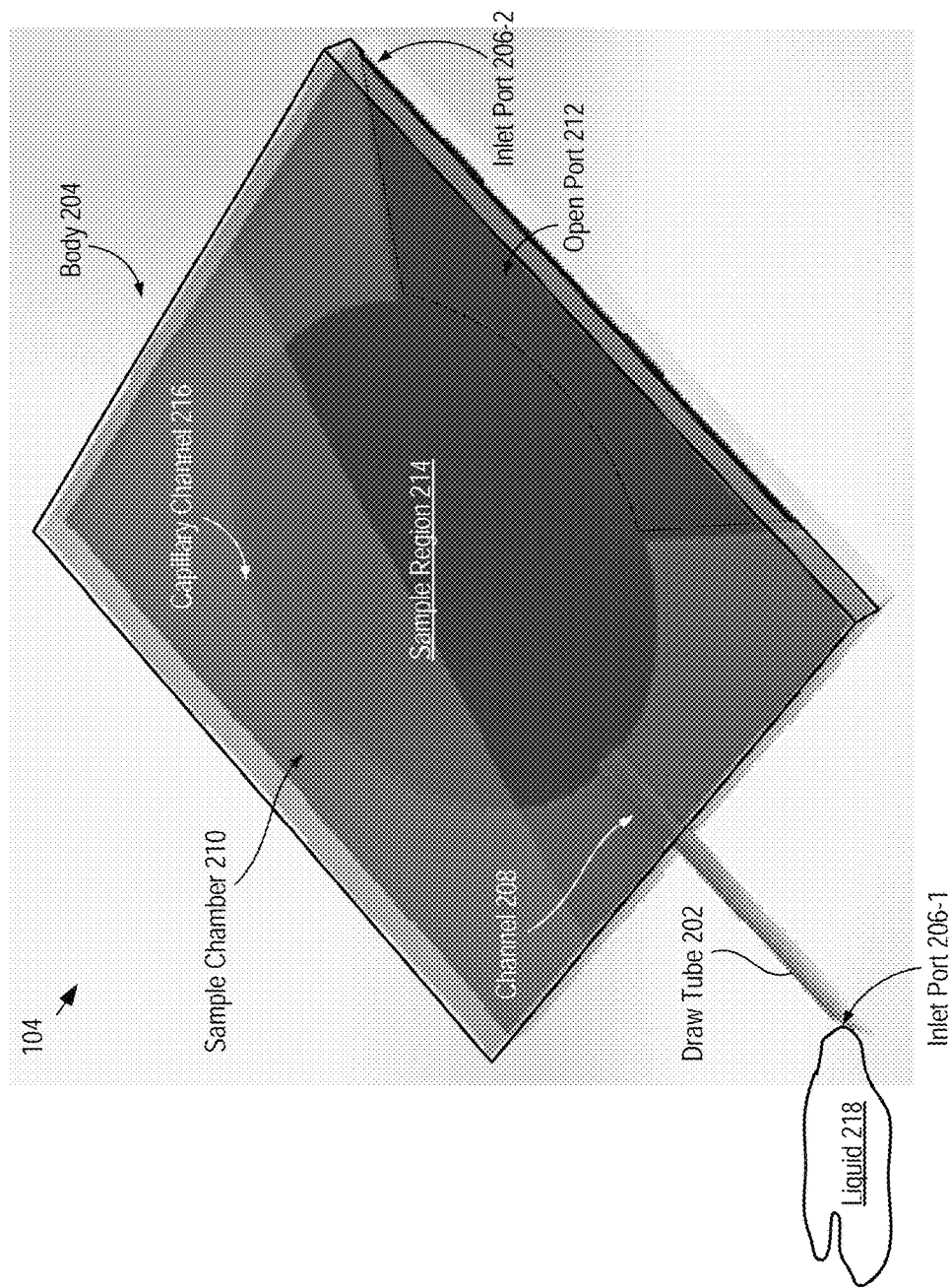

FIG. 1 depicts a schematic drawing of a sample holder in accordance with an illustrative embodiment of the present invention. Sample holder 100 is "microcuvette" operative for holding a minute volume of a liquid test sample. Sample holder 100 enables spectroscopic analysis of test sample 102 using mid-infrared radiation (i.e., radiation 104).

As discussed in U.S. Pat. No. 8,344,323, which is incorporated herein by reference, the use of mid-infrared radiation (MIR) for optical chemical analysis is highly desirable because it is rich with spectral absorption lines for many important chemicals and compounds materials. Due to this rich spectral content, MIR is often referred to as the "fingerprint region" of the spectrum.

In the prior art, however, MIR is not normally used for chemical analysis in spectrometry-based systems because most host materials (e.g., solvent fluids, blood, saline, bodily tissue, etc.) have a well-known absorption window in the mid-infrared wavelength range. Because of this absorption window, MIR does not significantly penetrate sample material in many applications, such as blood serum analysis, glucose monitoring, and the like.

Instead, prior-art spectroscopy systems are typically based on near-infrared light (i.e., wavelengths within the range of approximately 800 nm to approximately 2500 nm). Unfortunately, the spectral information characteristic of target chemicals and compounds in the sample material is typically overwhelmed by the background spectral content associated with host material in which the sample material is contained (e.g., water, which constitutes most of the material found in blood). In fact, the identification and quantitative analysis of target analytes and chemicals is often precluded by the fact that their signature information is simply "lost in the noise" of spectral information of the host material.

In the illustrative embodiment, sample holder 100 includes window regions 106 and 108, each which is transmissive for mid-infrared radiation (MIR). As a result, sample holder 100 enables radiation 104 to pass completely through the test sample to give rise to absorption signal 110 on the other side of the sample holder, where it can be detected and analyzed to determine the absorption characteristics of test sample 102 and identify its chemical composition. In some embodiments, the absorption spectra found in absorption signal 106 are compared against one or more chemical templates in a lookup table to facilitate the identification and quantification of specific chemicals and compounds.

In some embodiments, sample holder 100 includes only window region 106 and absorption signal 110 comprises light reflected by test sample 102.

FIGS. 2A-D depict schematic drawings of perspective, top, side, and front views, respectively, of sample holder 100. Sample holder 100 includes draw tube 202 and body 204.

Draw tube 202 is a hypodermic needle, typically comprising stainless steel, which has an outer diameter of approximately 125 microns, an inner diameter of approximately 50 microns, and a length of approximately 2.5 millimeters. Inlet port 206-1 is defined by the open end of draw tube 202, as indicated.

It should be noted that draw tube 202 can have any suitable outer diameter without departing from the scope of the present invention. It is an aspect of the present invention, however, that pain can be mitigated while extracting a bodily fluid (e.g., blood) from a patient by using a draw tube having an outer diameter that is less than the minimum separation between pain receptors at the location on the patient from which fluid is drawn (i.e., the draw site).

Nociceptive pain nerve receptors have a maximum density of 7-10 per mm (50-100 per $mm^2$)—even in the most sensitive parts of the human body. This gives that the minimum separation between pain receptors is generally within the range of approximately 100 microns to approximately 140 microns. By limiting the outer diameter of draw tube to a diameter less than or equal to the minimum separation of pain receptors at the draw site, the present invention enables a technician, an untrained assistant, or the patient themselves, to extract the fluid while causing little or no pain during the procedure. As a result, it is preferable that draw tube 202 have an outer diameter that is less than or equal to 140 microns. Conventional needles suitable for use in the present invention include, for example, ultra-thin, moshin-hair acupuncture needles, and the like. Note that this aspect of the invention is in contrast to conventional blood-drawing systems, which use approximately 250-micron diameter needles, as well as larger regular acupuncture needles, and conventional capillary blood lances, each of which can induce considerable pain. Draw tube 202, however, causes little or no pain and minimal distress on the surface or within body during draw and transfer to the sample chamber. Further, withdrawal of draw tube 202 does not result in external seepage and leaves no discernable stress to the body.

Body 204 is a structural element that includes channel 208, sample chamber 210, and open port 212.

Channel 208 is a conventional recess for locating draw tube 202. Channel 208 has a depth suitable for insertion of the draw tube into body 204 after its fabrication. The length of channel 208 is sufficient to provide mechanical stability to the draw tube assembly. Channel 208 locates draw tube 202 such that it is fluidically coupled with capillary channel 216.

Sample chamber 210 is a two-part cavity for containing test sample 102. Sample chamber 210 includes sample region 214 and capillary channel 216. By virtue of the use of MIR for optical analysis of test sample 102, only a short interaction length with a test sample is required to develop a high-quality analysis of the sample. As a result, the thickness of the sample chamber can be extremely small (typically, a few tens of microns) and, as result sample chamber 210 requires a total volume of only a few microliters (μL). Typically the volume of sample chamber 210 is within the range of approximately 0.2 μL to approximately 5 μL. In the depicted example, the volume of sample chamber 210 is approximately one microliter. It should be noted, however, that as long as the thickness of sample region 214 is kept small enough to give rise to sufficient capillary force, sample chamber 210 can have virtually any practical volume without departing from the scope of the present invention.

Open port 212 is a conduit for fluidically coupling sample chamber 210 with the environment outside sample holder 100. As a result, open port 212 enables egress of air from sample chamber 210 as fluid is drawn into sample holder 104. In some embodiments, draw tube 202 is not included and fluid is drawn into sample chamber 210 along inlet port 206-2, which is located at an edge of open port 212, while air is allowed to escape through the remainder of the open port.

It is another aspect of the present invention that sample holder 100 enables drawing of test sample 102 into sample chamber 210 without producing air bubbles in the liquid. The presence of bubbles in test sample 102 can interfere with its optical analysis. The development of air bubbles is especially detrimental for whole blood (or any other fluid) measurements in a photometric determination, for example. The presence of a large air bubble in the light path traversing the measurement zone results in overall measured values that are below the actual levels because a photometer interprets a bubble as a contributor to extremely low blood component concentrations. As a result, sample chamber 210 is dimensioned and arranged to mitigate the formation of bubbles fluid while being drawn.

Sample holder 100 is designed such that test sample 102 is loaded into sample chamber 210 via capillary force that is initiated by placing inlet port 206-1 into physical contact with liquid 218. The dimensions of draw tube 202 and capillary channel 216 are selected such that liquid 218 retains a meniscus as it passes from draw tube 202 to capillary channel 216 to sample region 214, as well as giving rise to a strong capillary force on the liquid such that it is rapidly drawn from inlet port 206-1 into sample chamber 210 without forming bubbles.

In some embodiments, the extremely small dimensions of draw tube 202 improves the ability of sample holder 100 to use capillary force to draw certain fluids, such as whole blood, by virtue of a significant decrease in its effective viscosity. This enables, among things, a significantly shorter bubble-free fill time for sample chamber 210. Specifically, Using a draw tube having an inner diameter within the range of approximately 10 microns to approximately 50 microns leads to "sheath flow" for the fluid within the tube, which reduces the its effective viscosity, thereby giving rise to a high capillary force on the liquid and enabling a higher flow rate through the draw tube. For the purposes of this Specification, including the appended claims, "sheath flow" is defined as a flow of a component-containing fluid that is characterized by a substantially component-free layer next to the tube wall and a flow core that consists primarily of the components. For example, sheath flow of whole blood is characterized by a substantially blood-cell-free flow region (primarily just plasma) near the tube wall that surrounds a flow core consisting mainly of blood cells.

Figure 3A:
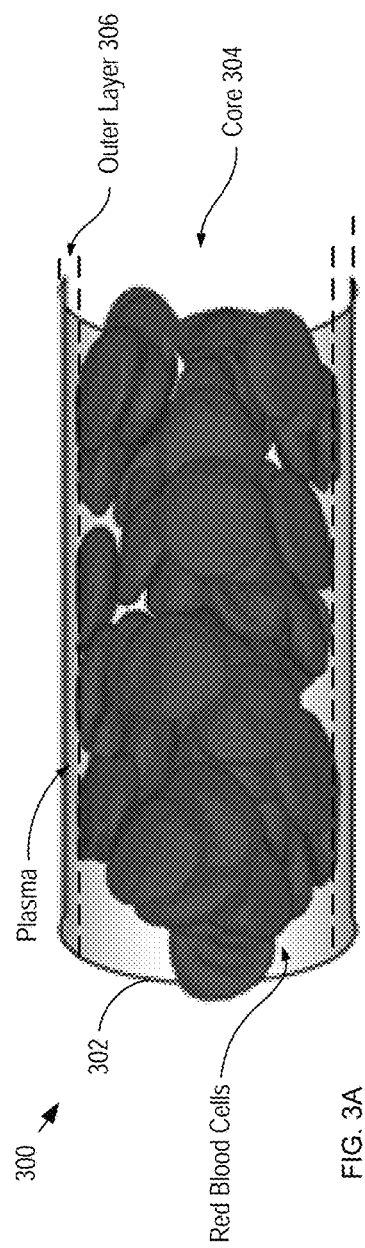
FIG. 3A depicts a schematic illustration of sheath flow within a small-inner-diameter conduit.

FIG. 3A depicts a schematic illustration of sheath flow within a small-inner-diameter conduit. Arrangement 300 includes conduit 302, through which whole blood flows.

Conduit 300 is analogous to draw tube 202 and has substantially the same dimensions (i.e., an inner diameter of approximately 50 microns). As shown in the drawing, red blood cells are concentrated in the center portion of conduit 302 to form core 304. Core is surrounded by outer layer 306, which includes mainly only plasma. Pure plasma has a lower viscosity compared with the RBC core, as well as whole blood in a bulk-flow condition. As a result, the plasma serves as a lubrication layer that reduces the effective viscosity of the blood. Further, in some cases, without the development of outer layer 306, suspended components, such as blood cells, could inhibit the retention of the meniscus at the forefront of liquid 218 as it is drawn into sample holder 100. As a result, in such cases, it is only the development of sheath flow that makes it possible to successfully draw liquid 218 through tube 202 and capillary channel 216 and completely fill sample region 214 with test sample 102.

Figure 3B:
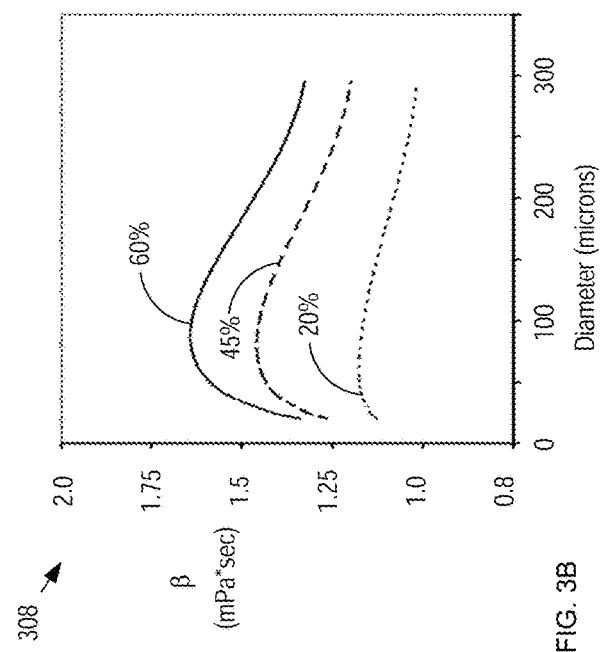
FIG. 3B depicts a plot of viscosity as a function of inner diameter of a conduit for whole blood having different volume percentages of red blood cells.

FIG. 3B depicts a plot of viscosity as a function of inner diameter of a conduit for whole blood having different volume percentages of red blood cells. Plot 308 shows that, beginning at inner diameters of about 75 microns, the effective dynamic viscosity, $\beta$, of whole blood drops dramatically as the inner diameter shrinks.

Plot 308 evinces that whole blood in conduit 300 has an effective dynamic viscosity of approximately 1.5 mPa*sec by virtue of its small circular cross-sectional area. As a result, the effective dynamic viscosity of whole blood in draw tube 202 is also 1.5 mPa*sec.

In similar fashion, the dimensions of capillary channel 214 are selected so that it enables development of even higher capillary pressure and, in some cases, lower effective viscosity. The dimensions of sample region 214 are larger than those of capillary channel 216, however, giving rise to a lower capillary pressure in this region, which mitigates bubble formation as liquid 218 fills the chamber.

Poiseuille's equation changes for a rectangular-section channel where instead of the $4^{th}$ power of radius, the dimensions contribute the $3^{rd}$ power of the smaller dimension and first power of the larger dimension (for sample chamber 210, these are 25 microns and 3 mm, respectively) for a flow rate of ~20 µL/sec. If sample chamber 210 were to be filled from a drop of blood introduced to the corner edge of the triangularly shaped capillary channel 216, for example, it would be filled in approximately 0.012 seconds. The 20 µL/sec flow rate represents a two orders of magnitude difference in throughput between draw tube 202 and sample chamber 210 at about the same driving capillary pressure. Essentially, the fluidic resistance of the draw tube is approximately one-hundred times higher than sample chamber 210. Since they are connected in series, the two will behave in a way dominated by the fluidic resistance of draw tube 202. The volume of the sample chamber is about 0.25 µL, so with a 0.1 µL/sec (capillary tube flow rate for effective blood viscosity) the sample chamber would be filled in about 2.5 seconds.

Figure 3C:
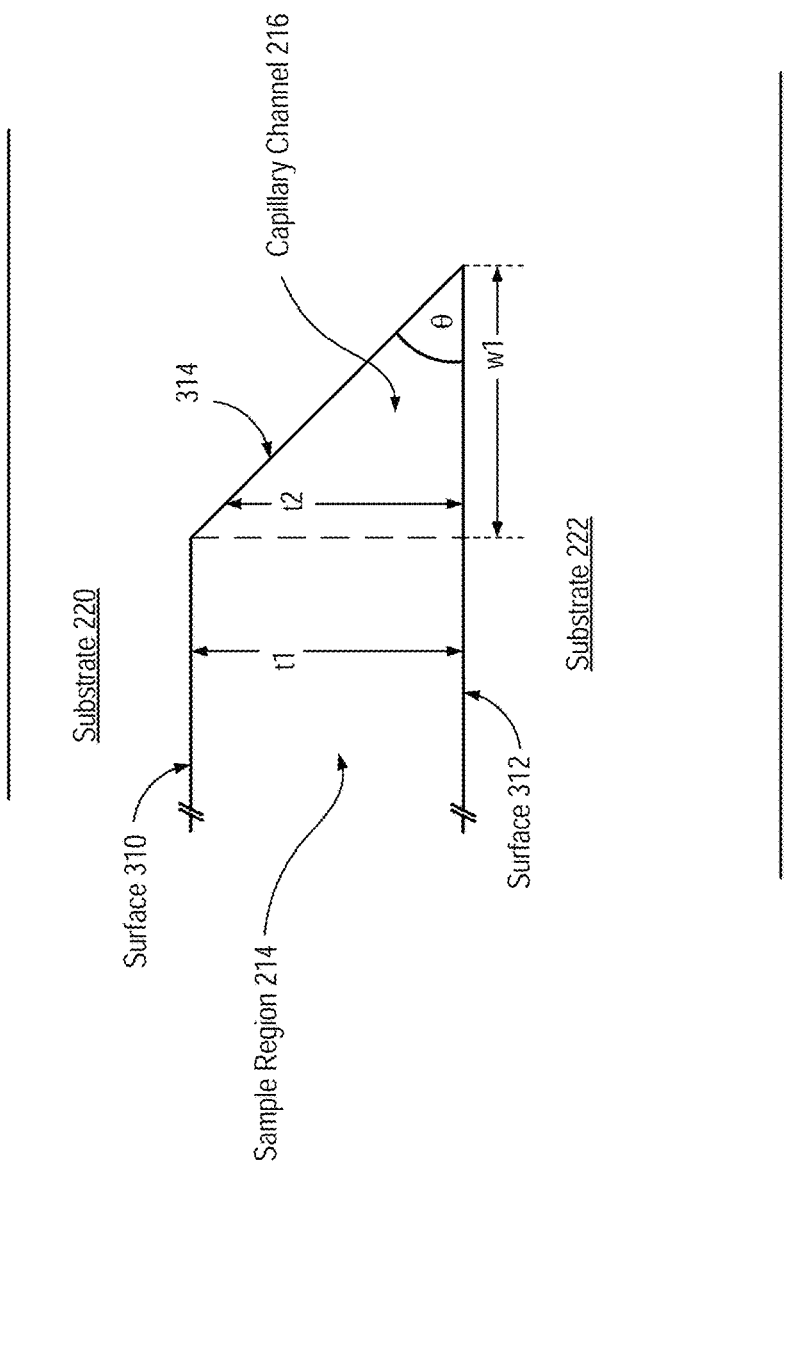
FIG. 3C depicts a schematic drawing of an enlarged cross-section of a portion of sample chamber 210.

FIG. 3C depicts a schematic drawing of an enlarged cross-section of a portion of sample chamber 210. FIG. 3C shows a cross-section taken through line a-a, as shown in FIG. 2B.

Sample region 214 is defined as the region of sample chamber 210 that is located between surfaces 310 and 312, which are substantially parallel. Surfaces 310 and 312 are separated by distance, t1, which is substantially uniform through the region. In the depicted example t1 is equal to 25 microns; however, any suitable value for t1 is within the scope of the present invention.

Capillary channel 216 is defined as the edge region of sample chamber 210, which is located between sidewall 314 and surface 312. In the depicted example, sidewall 314 is a substantially planar surface that is oriented at angle, $\theta$, with respect to surface 312, where $\theta$ is approximately 45°. As a result, capillary channel 216 is a triangularly shaped region having width, w1, of 25 microns. The thickness, t2, of capillary channel 216 is smaller than t1 and changes linearly from zero to t1 across the width, w1, of the capillary channel. In some embodiments, sidewall 314 is has a shape other than planar, such as curved. In such embodiments, however, thickness t2 still increases monotonically from zero to t1 across width w1.

By virtue of its smaller dimensions, the capillary force generated in capillary channel 216 is higher than that generated in sample region 214. Capillary channel 216 extends around the entire inner periphery of sample chamber 210 and is open to the atmosphere around sample holder 100 at open port 212, as described below.

The amount of capillary force available for drawing liquid 218 into sample chamber 210 to form test sample 102 can be determined by assuming maximal wetting at inlet port 206-1. This gives that the inner radius of draw tube 202 is the same as the radius of the meniscus of the liquid. Using Poiseuille's law for capillary pressure, in a tube having a circular cross-section with 0.05 mm internal diameter, the capillary pressure developed is 600 mm. Since draw tube 202 is fluidically coupled with triangularly shaped capillary channel 216, there is ample capillary pressure to feed the entire inner periphery of sample chamber 210, in both directions, to fill the entire chamber with liquid 218.

Throughput is linear with respect to the dynamic viscosity, however, so the result above should be scaled by a factor equal to the ratio of the viscosities of water and whole blood. The typical bulk dynamic viscosity of whole blood at 37° C. is 3 to 4 times that of water at 20° C.—specifically 3-4 mPa*sec, which would give the time required to fill sample chamber 210 with whole blood as 0.2 second.

Liquid 218 is drawn into sample chamber 210 until the chamber is completely full and the meniscus of the liquid reaches open port 212. Open port 212 is characterized by a significantly lower magnitude of capillary force imparted on liquid 218 due to the fact that it is characterized by a separation between its top and bottom surfaces that is too large to develop significant capillary force. As a result, once liquid 218 reaches the open port, the capillary force on liquid 212 drops off and the draw of the liquid into sample chamber 210 stops automatically.

Figure 3D:
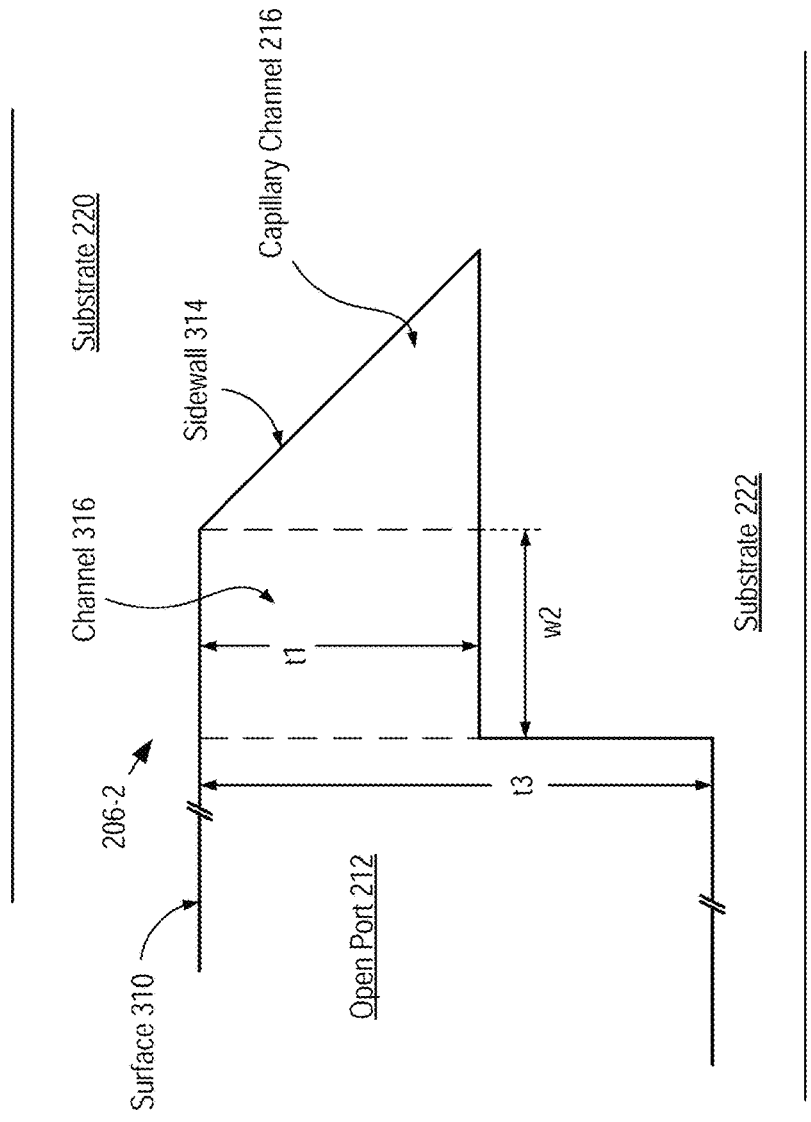
FIG. 3D depicts a schematic drawing of a portion of sample holder 104 that includes open port 212 and inlet port 206-2.

FIG. 3D depicts a schematic drawing of a portion of sample holder 104 that includes open port 212 and inlet port 206-2. FIG. 3D shows a cross-section of the sample holder taken through line b-b, as shown in FIG. 2B.

As seen in the figure, inlet port 206-2 includes capillary channel 216 and channel 316, which collectively enable drawing of liquid 218 into sample chamber 210 via capillary force.

Channel 316 has the same thickness, t1, as sample region 214, as described above. The width, w2, of channel 316 is selected to facilitate the development of sufficient capillary force to enable the filling of the sample chamber. Typically w2 is within the range of a few microns to a few hundred microns.

Channel 316 terminates at open port 212, which has a thickness t3. The value of thickness t3 is selected to be large enough to give rise to a capillary force that is too weak to draw liquid into sample chamber 210. In the depicted example, thickness t3 is approximately 100 microns; however, one skilled in the art will recognize, after reading this Specification, that t3 can have any suitable practical value.

Returning now to FIGS. 2A-D, body 204 comprises substrates 220 and 222, each of which comprises a material that is transmissive for MIR. In some embodiments, only one of the substrates is transmissive for MIR. Each of substrates 220 and 222 includes recessed features that collectively define channel 208, sample chamber 210, and open port 212.

Unfortunately, the material palette available in the prior art for use in window regions 106 and 108 is extremely limited due to typically poor transmittance across the 2.5 micron to 12.5 micron wavelength range. As a result, exotic materials, such as work-hardened silver halide and zinc selenide, have typically been used as structural materials in such components, as disclosed in U.S. Pat. No. 8,541,743, which is incorporated herein by reference.

It is yet another aspect of the present invention that the use of undoped float-zone silicon (FZS) provides significant advantages over the prior art. Specifically, and in contrast to generally held opinion, float-zone silicon, having a thickness of 500 microns or less, is transmissive out to far infrared wavelengths.

Figure 4:
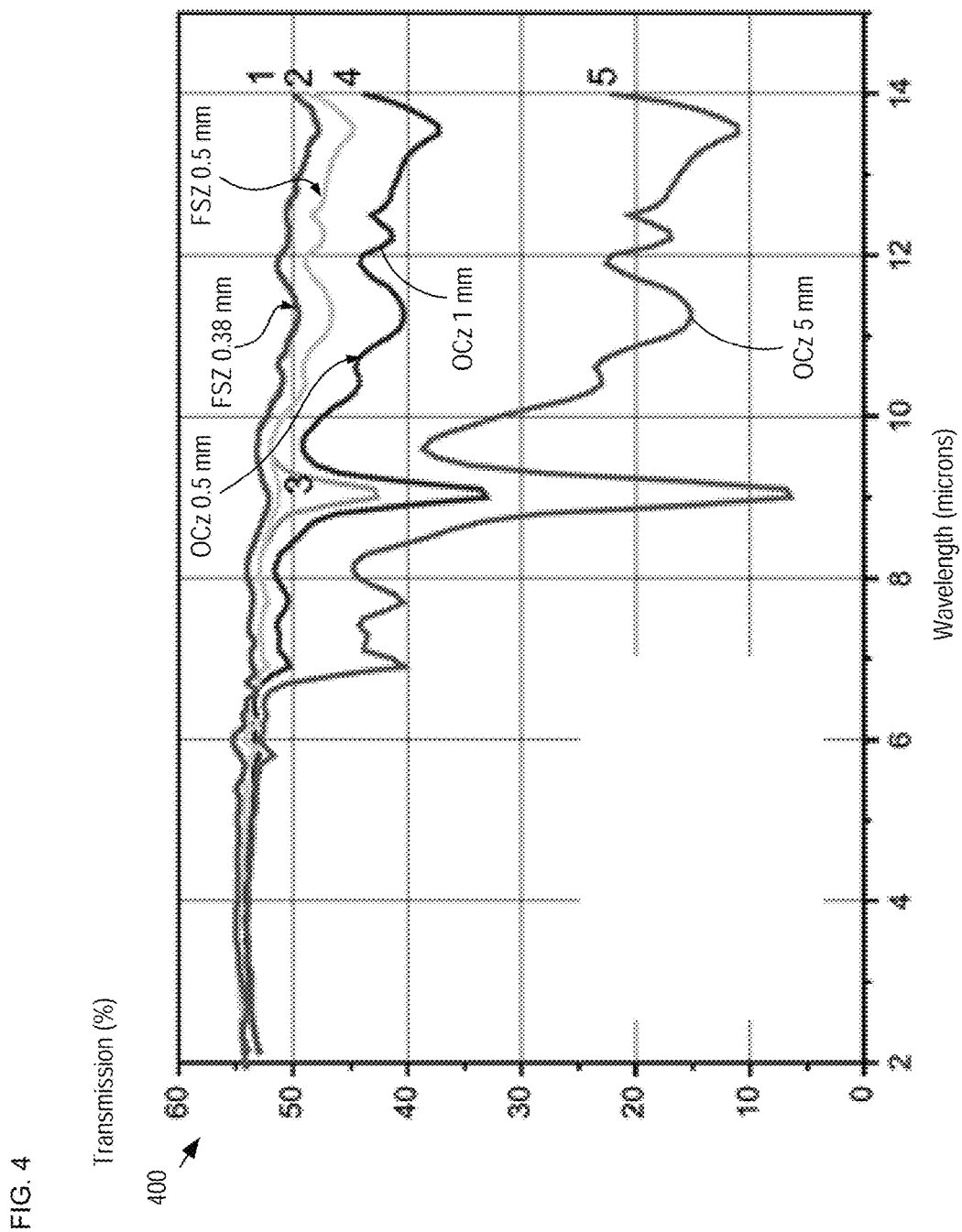
FIG. 4 depicts a plot of transmission for float-zone silicon and Czochralski-pulled silicon, at various thicknesses, over the range of wavelengths from 2 microns to 15 microns.

FIG. 4 depicts a plot of transmission for float-zone silicon and Czochralski-pulled silicon, at various thicknesses, over the range of wavelengths from 2 microns to 15 microns.

Plot 400 shows that the transmission through FZS, for thicknesses of 0.38 and 0.5 mm, remains above 45% over the mid-infrared range. The high transmission for FZS arises from the fact that, during the float zone refining process, substantially all impurities are eliminated, including substitutional dopants such as boron, phosphorus, arsenic, antimony and metallic impurities, and light impurities of oxygen and any carbon, by being pushed ahead of the melt region and reincorporated into the mono-crystalline ingot at much lower concentrations.

For Czochralski-pulled Silicon (OCz-Si), however, large absorption bands are seen at approximately 9-micron wavelength for each tested thickness (i.e., 0.5 mm, 1 mm, and 5 mm). The absorption band is due to oxygen impurities in the material. It should be noted that there is also a smaller absorption band at approximately 5.8 microns, which are due to the presence of other dopants in the material.

For operation in the MIR, it is critical that window regions 106 and 108 do not substantially absorb light signal 104. FZS is both transmissive for MIR, readily available, and easy to handle and process. Although other MIR-transmissive materials, such as Silver Halides and Zinc Selenide, can be used in embodiments of the present invention, these materials are exotic and expensive, and they are difficult to handle and incorporate into a body 204. As a result, FZS is preferably used for window regions 106 and 108.

Because of the ease of etching FZS, body 204 can be fabricated using conventional planar processing techniques. In the depicted example, body 204 is fabricated in three steps.

First, substrate 220 is etched to a depth of 25 microns (i.e., depth t1) in sample region 214 and the region of channel 208. One skilled in the art will recognize that, with the use of the proper etching technology, this operation also forms sidewall 216. In some embodiments, sidewall 216 is formed or further shaped in a subsequent etch or grinding operation.

Second, substrate 222 is etched to a depth of approximately 100 microns in the regions of channel 208 and open port 212. This depth is selected to provide a total height of channel 208 of 125 microns once substrates 220 and 222 are joined to complete body 204, as discussed below.

It should be noted that, while embodiments of the present invention provide particular advantage to systems for interrogating a test sample with mid-infrared radiation, aspects of the present invention afford advantages in systems that interrogate test samples with radiation of other wavelengths, such as visible light, x-ray radiation, etc. As a result, in some embodiments, one or both of window regions 106 and 108 comprise a material that is transmissive for other wavelengths, such as glass, plastic, quartz, composite materials, and the like. In some embodiments, one or both of window regions 106 and 108 is an element formed separately from body 204 and then affixed to the body.

Figure 5:
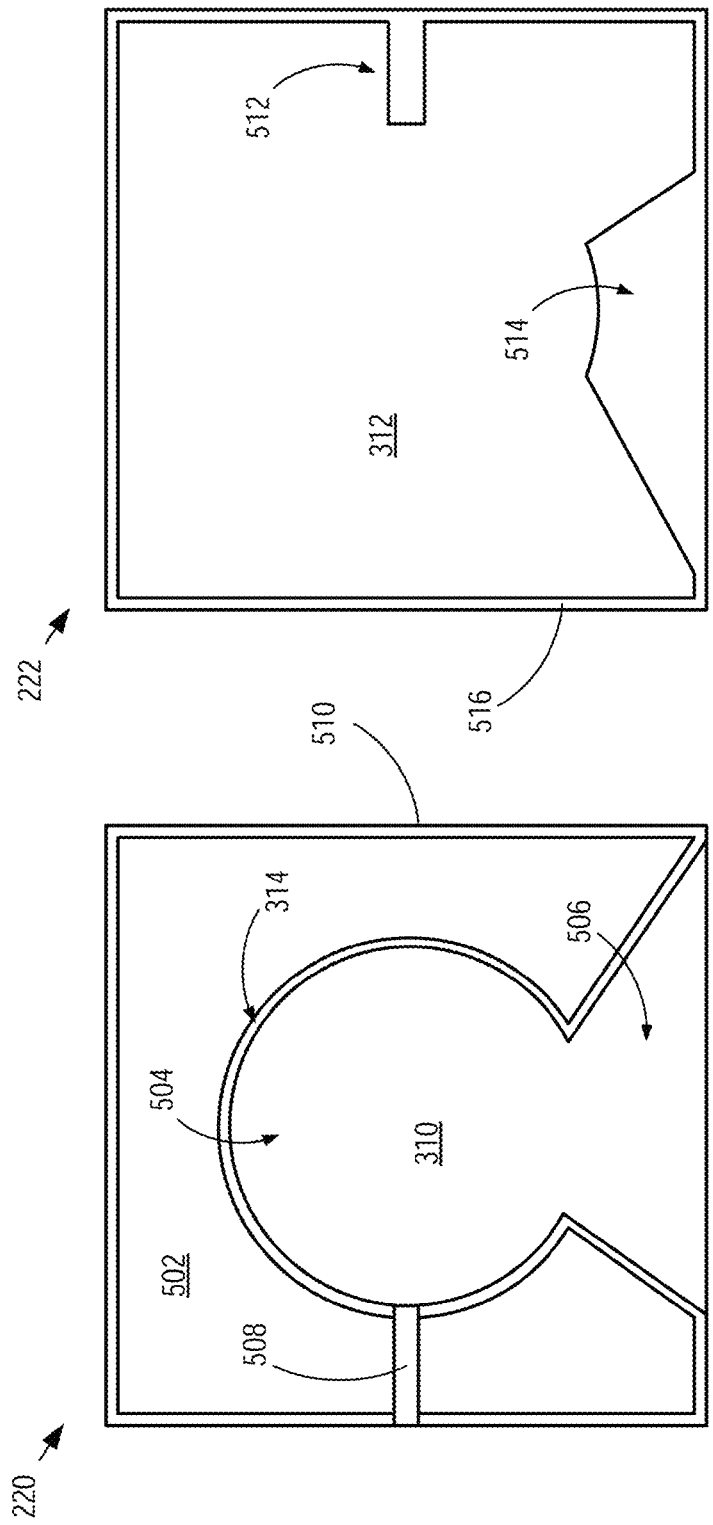
FIGS. 5A-B depict top views of substrates 220 and 222, respectively, after the completion of etching to define their features.

FIGS. 5A-B depict top views of substrates 220 and 222, respectively, after the completion of etching to define their features.

Substrate 220 is fabricated in two etch steps. First, nascent sample chamber 504 and nascent port region 506 are etched to a depth of t1 from the original surface of the substrate (i.e., surface 502). The formation of nascent sample chamber 504 and nascent port region 506 exposes surface 310, which defines the top surface of sample region 214, as described above.

A second etch is then used to define nascent channel region 508 and nascent scribe line 510. Typically, these features are etched to a depth that is substantially equal to the outer diameter of draw tube 202. As a result, in the depicted example, these features are etched to a depth of approximately 63 microns.

In similar fashion, substrate 222 is etched to a depth of approximately half the outer diameter of draw tube 202 (i.e., 63 microns) from its original top surface (i.e., surface 312) to define nascent channel region 512, nascent open port region 514, and nascent scribe line 516.

Once the fabrication of each of substrates 220 and 222 is complete, one of the substrates is flipped over to mate surfaces 312 and 502, which are permanently joined using a conventional joining method, such as oxygen-assisted plasma bonding, thermos-anodic bonding, fusion bonding, an adhesive layer, and the like. This completes channel 208, sample chamber 210, and open port 212. The individual die are then singulated and draw tube 202 is inserted into channel 208 and affixed to complete sample holder 100. Because each of nascent channels 508 and 512 have a depth of approximately half the outer diameter of draw tube 202, the center of the draw tube is substantially aligned with the center of sidewall 314.

Once fully formed individual bodies 204 are singulated from the multi-die substrates. To facilitate die singulation, in the depicted example, nascent scribe line 510 is formed around the perimeter of the region of body 204 on substrate 220.

One skilled in the art will recognize that FIGS. 5A-B depict individual die of a plurality of sample holder die formed simultaneously on each substrate. Typically, integrated-circuit die are singulated from a processed wafer by sawing through the wafer between the die. This would create significant particulate issues for embodiments of the present invention, however, and is preferably avoided. The addition of scribe lines 510 and 516 on substrates 220 and 222, respectively, enable singulation of the individual die by concentrating fracture strain in the regions of the scribe lines. As a result, the individual die can be singulated without minimal particulate generation.

In some embodiments, a heater is included within sample chamber 210 to enable evaporation of the background solvent of test sample 102 through open port 212 while inlet port 206-1 is in contact with liquid 218. Such embodiments enable an increase in the concentration of constituent solutes in the test sample by inducing additional capillary inflow as the solvent is removed.

Figure 6:
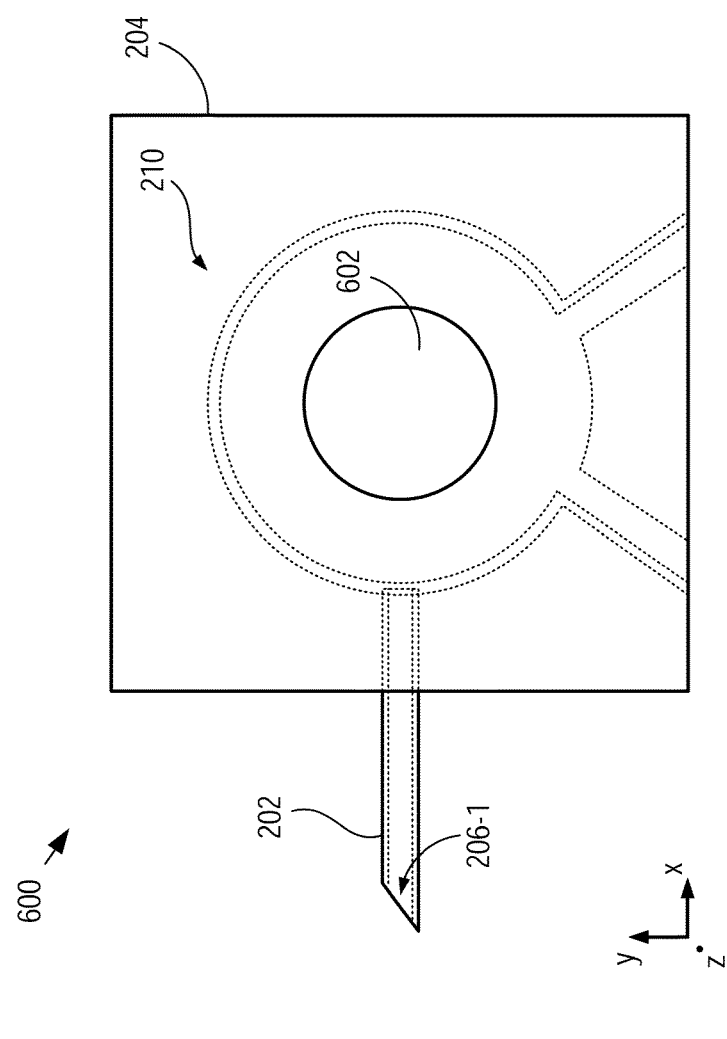
FIG. 6 depicts a schematic drawing of a sample holder in accordance with a first alternative embodiment of the present invention.

FIG. 6 depicts a schematic drawing of a sample holder in accordance with a first alternative embodiment of the present invention. Sample holder 600 is analogous to sample holder 100; however, sample holder 600 includes optical element 602, which is disposed on window region 106 to enable an optical function to be performed on radiation 104.

Optical element 602 is a refractive lens for collimating radiation 104. In some embodiments, optical element 602 is another optical element, such as a microlens array, a diffraction grating, a holographic element, a Fresnel zone plate, a Bragg grating, a prism, and the like. In some embodiments, an optical element is disposed on each of window regions 106 and 108.

Figure 7:
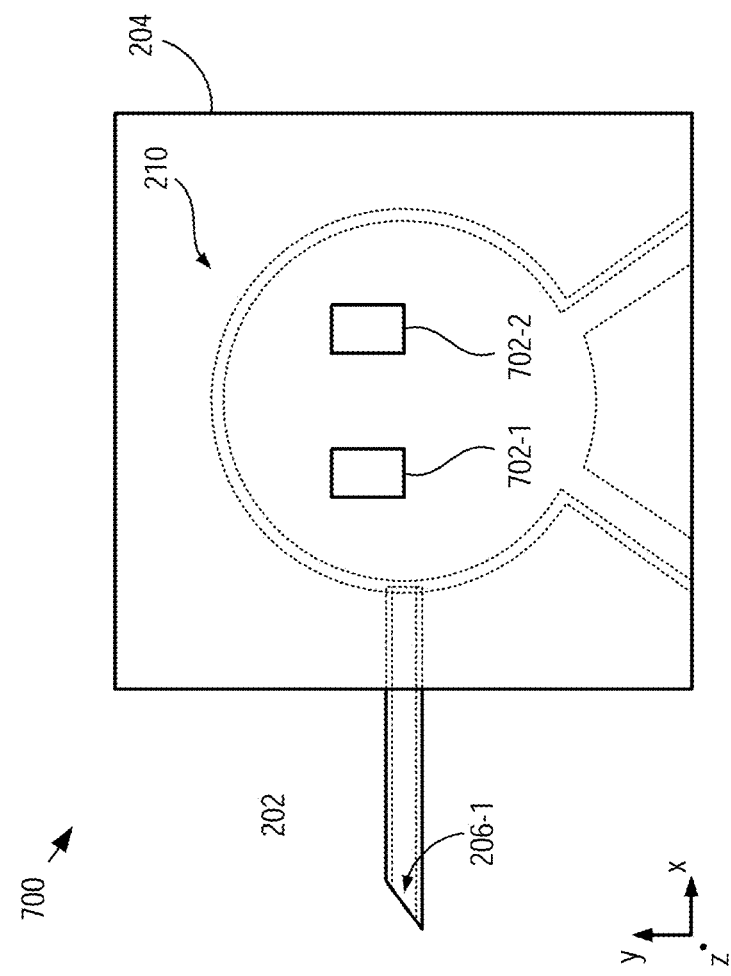
FIG. 7 depicts a schematic drawing of a sample holder in accordance with a second alternative embodiment of the present invention.

FIG. 7 depicts a schematic drawing of a sample holder in accordance with a second alternative embodiment of the present invention. Sample holder 700 is analogous to sample holder 100; however, sample holder 700 includes regions 702-1 and 702-2, each of which includes a dry reagent that can mix and chemically react with test sample 102 to produce an optical effect, such as a color change, that is observable through window region 106. In some embodiments, one or more of regions 702 is located within a micro channel that isolates its reaction from other regions of sample chamber 210. As a result, multiple, simultaneous independent observations are enabled.

In some embodiments, accurate measurement of ion concentration in test sample 102 is desired. Such analysis is critical in many clinical settings, such as neonatal care. In the prior art, such ion measurement is performed via a complex and expensive method, such as atomic absorption or flame emission spectroscopy. The present invention enables low-cost, simple electrochemical methods for measuring ion concentrations within sample region 102.

Figure 8:
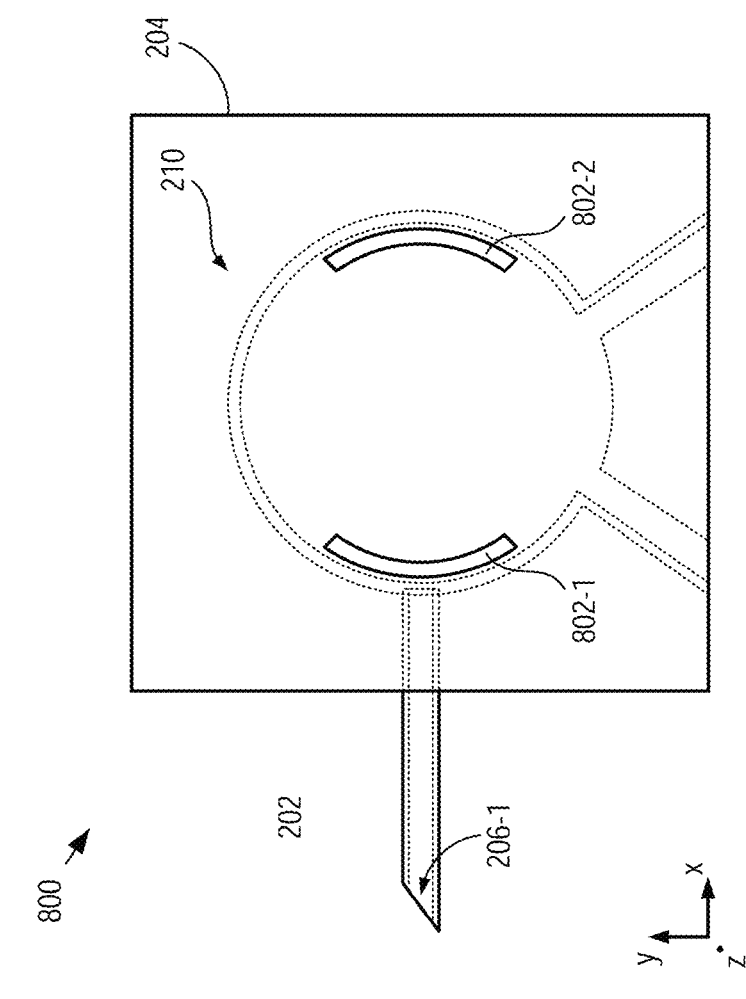
FIG. 8 depicts a schematic drawing of a sample holder in accordance with a third alternative embodiment of the present invention.

FIG. 8 depicts a schematic drawing of a sample holder in accordance with a third alternative embodiment of the present invention. Sample holder 800 is analogous to sample holder 100; however, sample holder 800 includes electrodes 802-1 and 802-2, which are electrically independent of one another, as well as draw tube 202.

In some embodiments, the resistance between electrodes 802-1 and 802-2 is monitored and used as an indicator of the ionic content of test sample 102.

The inclusion of electrodes 802-1 and 802-2 also enables the use of Faraday's principle to "electro-plate" different ions electrochemically onto each of electrodes 802-1 and 802-2. One skilled in the art will recognize that different ions require different electrochemical potentials to plate. As a result, by biasing each of electrodes 802-1 and 802-2 with a different voltage relative to, for example, draw tube 202, each electrode selectively plates a different ion, independent determination of the concentration for each ion is enabled. In some embodiments, sample holder 800 includes a different number of electrodes 802.

Electroplating to completion is difficult and very time-consuming using large volumes of solution. Since the volume of test sample 102 is so small, however, such electrolytic analysis can be performed rapidly.

System 800 enables measurement of the blood chemical parameters of, for example, sodium (132-140 mg/dl), potassium (3.5-6 mg/dl), calcium (8-10 mg/dl) and pH (7.3-7.45). Further, pure salts can be evaluated in system 800 one at a time and through a range of spiked concentrations. Then all salts will be evaluated by sensor simultaneously.

In some embodiments, electronic circuitry instead of, or in addition to, electrodes 802, such as integrated circuit devices, are included in body 204. As a result, sample holder 800 can include capabilities such as wireless communication, signal amplification and pre-processing, signal processing, sample analysis, and the like. Further, in some embodiments, the electronic circuitry can enable remote powering of such circuitry via inductive power coupling.

In some embodiments, a microfluidic device or system is included in sample chamber 210 to enable manipulation of different portions of test sample 102.

Figure 9A:
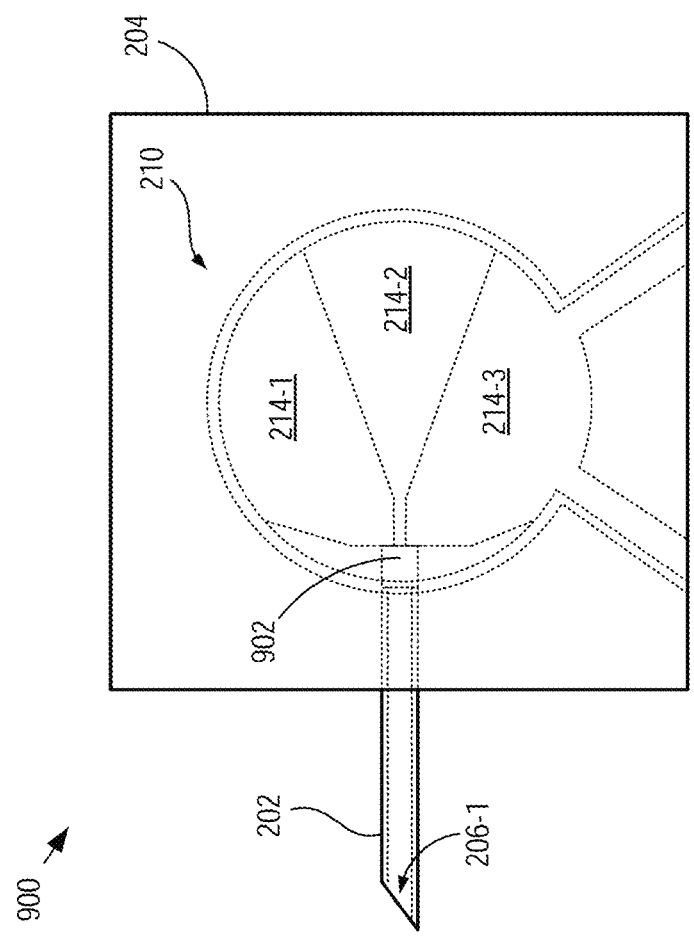
FIG. 9A depicts a schematic drawing of a sample holder in accordance with a fourth alternative embodiment of the present invention.

FIG. 9A depicts a schematic drawing of a sample holder in accordance with a fourth alternative embodiment of the present invention. Sample holder 900 is analogous to sample holder 100; however, sample holder 900 includes a plurality of sample regions 214-1 through 214-3, and microfluidic system 902. In the depicted example, microfluidic system 902 is a cross-flow filtration system that physically segregates constituents of whole blood and provides a different test sample within each of sample regions 214. As a result, each test sample can be individually characterized using, for example, mid-infrared spectroscopy.

FIG. 9B depicts a schematic drawing of microfluidic system 902. Microfluidic system 902 includes inlet port 904, channels 906-1 through 906-3, filters 908 and 910, and outlet ports 912-1 through 912-3. Microfluidic system 902 enables embodiments of the present invention to segregate cells by size, which can be used to monitor concentrations of abnormal blood cells, etc.

System 902 exploits the fact that red blood cells (RBCs) and white blood cells (WBCs) are significantly different sizes. RBCs are typically 6-8 micron diameter donut-shaped structures with thickness of 2-2.5 microns and a minimum thickness at their center of 0.8-1 micron. WBCs are more spherically shaped with a have a diameter distribution of approximately 10-20 microns for about 85% of the cells and approximately 7-8 microns for about 15% of the cells.

Filter 908 is located in the sidewall between channels 906-1 and 906-2. Filter 908 is characterized by filter pores of approximately 5 microns distributed uniformly along the filter. As blood flows across its surface, WBCs are blocked from passing through filter 908 due to their size. As a result, WBCs remain in channel 906-1 and flow to outlet port 912-1. Outlet port 912-1 is fluidically coupled with sample region 214-1. As a result, sample region 214-1 is loaded with a test sample rich in white blood cells. RBCs and plasma readily pass through filter 908 into channel 906-2.

Filter 910 is located in the sidewall between channels 906-2 and 906-3. Filter 910 is characterized by filter pores of approximately 1.5 microns, which are distributed uniformly along the filter. As RBCs and plasma flows through channel 906-2 and across the surface of filter 910, RBCs are blocked from passing through filter 910 due to their size. As a result, RBCs remain in channel 906-2 and flow to outlet port 912-2. Outlet port 912-2 is fluidically coupled with sample region 214-2. As a result, sample region 214-2 is loaded with a test sample rich in red blood cells. It should be noted that, while sickle-cell diseased red blood cells have an altered donut shape, these cells still have thicknesses of 2-2.5 microns and are also prevented from passing through filter 910.

Plasma passes through filter 910 into channel 906-3 to be carried to outlet port 912-3 to load sample region 214-3 with a test sample that is substantially pure plasma.

In some embodiments, microfluidic system 902 includes microfluidic devices other than filters, such as mixers, heaters, separation elements, and the like. It will be clear to one skilled in the art, after reading this Specification, how to make and use alternative embodiments of the present invention wherein microfluidic system 902 includes any practical microfluidic device, or a portion of a larger microfluidic system.

It is to be understood that the disclosure teaches just some examples of embodiments in accordance with the present invention and that many variations of the invention can easily be devised by those skilled in the art after reading this disclosure and that the scope of the present invention is to be determined by the following claims.

What is claimed is:

1. A sample holder for holding a test sample, the sample holder comprising:
    an inlet port; and
    a sample chamber that includes a first window region that is transmissive for a first radiation that is characterized by a wavelength within the range of 2.5 microns to 12.5 microns, the sample chamber having a sample region and a capillary channel that that extends around at least half the perimeter of the sample region, wherein the capillary channel fluidically couples the inlet port and the sample region;
    wherein the sample region is characterized by a first capillary force for a first liquid and the capillary channel is characterized by a second capillary force for the first liquid, and wherein the second capillary force is higher than the first capillary force such that the capillary channel is operative for drawing the first liquid from the inlet port to the sample chamber to entirely fill the sample region with the first liquid; and
    wherein the first liquid includes the test sample.

2. The sample holder of claim 1 further comprising a body that includes:
    the first window region, the first window region having a first surface;
    a second surface comprising a second window region being transmissive for the first radiation, the second surface being parallel with the first surface; and
    a sidewall that extends from the first surface to the second surface;
    wherein the first surface and second surface collectively define the sample region, and wherein the sample region has a first thickness; and
    wherein the first surface, the second surface, and the sidewall collectively define the capillary channel such that the capillary channel has a first width and a second thickness that changes monotonically from zero to the first thickness along the first width.

3. The sample holder of claim 2 wherein the sidewall forms an angle that is equal to or less than 45° with one of the first surface and second surface.

4. The sample holder of claim 2 wherein the body further comprises an optical element.

5. The sample holder of claim 2 wherein the body further comprises a microfluidic system, the microfluidic system being located within the sample chamber.

6. The sample holder of claim 2 wherein the body further comprises a reagent, the reagent being located within the sample chamber.

7. The sample holder of claim 1 wherein the first window region comprises float-zone silicon.

8. The sample holder of claim 1 further comprising a draw tube that includes the inlet port, the draw tube having an outer diameter that is less than the minimum spacing of pain receptors at a draw site.

9. The sample holder of claim 1 wherein the inlet port is dimensioned and arranged to enable sheath flow of the sample from the inlet port to the sample chamber.

10. A method comprising:
    providing a sample holder for a test sample, the sample holder including a body comprising a first window region that is transmissive for mid-infrared radiation, and the sample holder having an inlet port and a sample chamber that includes a sample region and a capillary channel that extends around at least half the perimeter of the sample region, wherein the capillary channel fluidically couples the inlet port and the sample region; and establishing physical contact between the inlet port and a liquid that contains the test sample;

wherein physical contact between the inlet port and the liquid gives rise to a capillary force that draws the test sample into the sample chamber via the capillary channel to entirely fill the sample region with the liquid.

11. The method of claim 10 wherein the sample holder is provided by operations comprising:

forming a first cavity in a first substrate comprising the first window region, the first cavity including a sidewall and a first surface that is planar; and joining the first substrate and a second substrate that includes a second window region having a second surface, wherein the first surface, second surface, and sidewall collectively define the sample chamber such that the sample region is characterized by a first capillary force for the first liquid and the capillary channel is characterized by a second capillary force for the first liquid, and wherein the second capillary force is higher than the first capillary force.

12. The method of claim 10 wherein the first window region comprises float-zone silicon.

13. The method of claim 10 wherein the sample holder is provided such that it further includes a draw tube that comprises the inlet port and a second port that is fluidically coupled with sample region via the capillary channel, and wherein the draw tube has an outer diameter that is less than the minimum separation of pain receptors at a draw site.

14. The method of claim 13 wherein the outer diameter is less than or equal to 140 microns.

15. The method of claim 10 further comprising increasing the concentration of an analyte within the sample region by evaporating a solvent, the test sample including the solvent and the analyte.

16. The method of claim 10 further comprising reacting a reagent with the test sample in a first region that is within the sample chamber.

17. The method of claim 10 wherein the sample holder is provided such that it further includes an optical element.

18. The method of claim 10 wherein the sample holder is provided such that the sample chamber includes at least a portion of a microfluidic system.

19. The method of claim 10 further comprising:

providing a first electrode that is located within the sample chamber; and providing an electric field having a first magnitude between the first electrode and a second electrode, wherein the electric field traverses at least a portion of the test sample;

wherein the magnitude of the electric field is based on the electrochemical potential required to electroplate a first analyte.

* * * * *